United States Patent
Eustache et al.

(10) Patent No.: US 7,396,953 B2
(45) Date of Patent: Jul. 8, 2008

(54) ANGIOGENESIS INHIBITORS AND PHARMACEUTICAL/COSMETIC APPLICATIONS THEREOF

(75) Inventors: Jacques Eustache, Mulhouse (FR); Pierre Van De Weghe, Baldersheim (FR); Vincent Rodeschini, Mulhouse (FR); Celine Tarnus, Rixheim (FR)

(73) Assignees: Galderma Research & Development, Biot (FR); CNRS, Paris (FR)

( * ) Notice: Subject to any disclaimer, the term of this patent is extended or adjusted under 35 U.S.C. 154(b) by 1 day.

(21) Appl. No.: 11/642,846

(22) Filed: Dec. 21, 2006

(65) Prior Publication Data

US 2007/0167519 A1 Jul. 19, 2007

Related U.S. Application Data

(63) Continuation of application No. PCT/FR2005/001656, filed on Jun. 29, 2005.

(30) Foreign Application Priority Data

Jun. 30, 2004 (FR) .................... 04 07235

(51) Int. Cl.
*C07C 69/76* (2006.01)
*C07C 49/00* (2006.01)
*A01N 37/10* (2006.01)

(52) U.S. Cl. .............. 560/61; 560/55; 560/64; 568/376; 514/532

(58) Field of Classification Search ................. 568/376, 568/425, 715, 822; 560/465, 471, 493
See application file for complete search history.

(56) References Cited

U.S. PATENT DOCUMENTS 6,803,382 B2 10/2004 Eustache et al.

FOREIGN PATENT DOCUMENTS

WO   WO 03/040119 A1   5/2003

OTHER PUBLICATIONS http://www.medicinenet.com/rosacea/article.htm last visited on May 10, 2007.*
Rodeschini et al., Journal of Organic Chemistry (2005), 70(6), 2409-2412.*
Rodeschini et al., "Enantioselective Approaches to Potential MetAP-2 Reversible Inhibitors", XP-002352284, J. Org. Chem., 2005, pp. 2409-2412, vol. 70, American Cancer Society, published on Web Feb. 18, 2005.
Rodeschini et al., "MetAP-2 Inhibitors Based on the Fumagillin Structure, Side-Chain Modification and Ring-Substituted Analogues", XP-002329329, J. Org. Chem., 2004, pp. 357-373, vol. 67, American Cancer Society, published on Web Dec. 23, 2003.
Zhou et al., "Fumagalone, a Reversible Inhibitor of Type 2 Methionine Aminopeptidase and Angiogenesis", XP-002329330, J. Med. Chem., 2003, pp. 3452-3454, vol. 46, American Cancer Society, published on Web Jul. 9, 2003.

* cited by examiner

*Primary Examiner*—Karl Puttlitz
(74) *Attorney, Agent, or Firm*—Buchanan, Ingersoll & Rooney, PC

(57) ABSTRACT

Novel derivatives of fumagalone have the general formula (I):

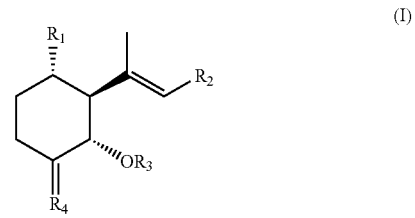

and are useful angiogenes is inhibitors; these can be formulated into pharmaceutical compositions suited for human or veterinary medicine, or can be formulated into cosmetic compositions.

11 Claims, 3 Drawing Sheets

10

11

12

18

17

14

ANGIOGENESIS INHIBITORS AND PHARMACEUTICAL/COSMETIC APPLICATIONS THEREOF

CROSS-REFERENCE TO PRIORITY/PCT APPLICATIONS

This application claims priority under 35 U.S.C. § 119 of FR 04/07235, filed Jun. 30, 2004, and is a continuation of PCT/FR 2005/001656, filed Jun. 29, 2005 and designating the United States (published in the French language on Feb. 2, 2006 as WO 2006/010859; the title and abstract were also published in English), each hereby expressly incorporated by reference and each assigned to the assignee hereof.

BACKGROUND OF THE INVENTION

1. Technical Field of the Invention

The present invention relates to novel fumagalone compounds, as novel and useful industrial products. This invention also relates to their method of preparation and to their formulation into pharmaceutical compositions suited for administration in human or veterinary medicine, or formulated into cosmetic compositions.

2. Description of Background and/or Related and/or Prior Art

As is well known, angiogenesis is the formation of new blood vessels from existing vessels. Angiogenesis plays an important role in the development of the tissues of the embryo but hardly ever occurs in healthy adult tissues.

The development of new blood vessels may be observed in non-physiological conditions. This development can be beneficial, for example in the case of cicatrization. But its action is generally harmful: development of tumors, or accompanying chronic inflammatory diseases.

The role of angiogenesis is most evident in the case of tumors: it has been demonstrated that, in the growth phase, the development of new blood vessels was absolutely essential for tumors.

Although the link from development of a tumor and angiogenesis was suggested by Folkman more than thirty years ago (Folkman, J., *New. Engl. J. Med.*, 1971, 285, 1182), it is only in the last ten years or so that the possibility of anti-tumor therapies based on control of angiogenesis has been widely accepted. At the present time, numerous anti-angiogenic molecules are under clinical investigation (Norrby, K., *APMIS*, 1997, 105, 417-437; Arbiser, J. L., *J. Am. Acad. Dermatol.*, 1996, 34(3), 486-497; Fan, T-P. D., *TIPS*, 1995, 16, 57-66). As was shown recently (Boehm, T., Folkman, J. et al. *Nature*, 1997, 390, 404-407), an anti-tumor therapy based on control of angiogenesis is less likely to result in the appearance of resistance phenomena.

Angiogenesis is also associated with the pathological process of various inflammatory diseases. Accordingly, inhibition of angiogenesis can have implications for the treatment and prevention of these diseases. Thus, abnormal angiogenesis is involved in various diseases of an inflammatory nature.

Many groups of researchers have attempted to discover novel molecules capable of inhibiting angiogenesis, for example Taylor by using protamine (Taylor, S. et al., *Nature*, 1982, 297, 307) or the use of heparin in the presence of cortisone by Folkman (Folkman, J. et al., *Science*, 1983, 221, 719).

In dermatology, it is very widely accepted that a problem with control of angiogenesis is associated with a great many disorders: tumors, haemangiomas (excessive angiogenesis) (Creamer, D. et al., *Br. J. Dermatol.*, 1997, 136 (6), 859-865; Jackson, J. R. et al. *FASEB. J.*, 1997, 11(6), 457-465), ulcers (deficient angiogenesis).

To date, steroids have been used for the treatment of haemangiomas, and their efficacy is probably due to their anti-angiogenic activity.

It is also apparent that angiogenesis is receiving increased attention as a target for therapeutic intervention in other dermatologic disorders. This is evident at the clinical level, for example, from the design of studies focusing on angiogenesis (Gradishar, W. J. *Invest New Drugs*, 1997, 15(1), 49-59) and from the increasing number of reports, articles and publications referring to angiogenesis (*Angiogenesis. Rep. Med. Chem.*, 1997, 32, 161-170; *Angiogenesis. Rep. Med. Chem.*, 1992, 27, 139-148).

Finally, it should be noted that various classes of molecules with dermatological activity (retinoids, vitamin 1,25-di-OH-D-3) are now being examined for their potential role in angiogenesis (*Eur J. Pharmacol.*, 1993, 249 (1), 113-116; *Cancer Lett.*, 1995, 89 (1) 117-124).

In the field of angiogenesis, fumagillin and derivatives thereof occupy a special place: TNP-470 (AGM 1470) described in EP-0-357,061 and its successor, FR-118847 described in EP-0-386,667, are active in many models of angiogenesis and have a recognized anti-tumor activity (Logothetis, C. J., *Clin Cancer Res.*, 2001 May; 7(5):1198-1203).

These compounds are described as having activity in inhibition of angiogenesis, suppression of cellular proliferation and immunosuppression.

These compounds are synthesized by conventional methods of hemisynthesis as described in EP-0-357,061 and EP-0-386,667 cited above.

Other derivatives of fumagillin, such as the 6-epifumagillols described in EP-0-387,650, also have applications in inhibition of angiogenesis, suppression of cellular proliferation and immunosuppression. Once again, they are synthesized by a hemisynthetic method.

The mode of action of these compounds remained unexplained until 1997, when a biological target, a methionine aminopeptidase: MetAP-2, was identified (Griffith, E. C. et al. *Chem. Biol.*, 1997, 4(6), 461-471). The inhibitory activity of various derivatives of fumagillin on this enzyme displays good correlation with the anti-angiogenic effect.

The discovery of this enzyme permitted better targeting of research activity and synthesis of novel analogues of fumagillin having better biological activity while reducing their side-effects. In particular, the mode of action proposed by Griffith, Liu and Clardy (a; Liu, S. et al. *Science*, 1998, 282, 1324-1327. b; Griffith, E. C. et al. *Proc. Natl. Acad. Sci. USA*, 1998, 95, 15183-15188) for fumagillin and its analogues involves crucial interaction from the exocyclic epoxide of these molecules and a cobalt atom located at the active site of MetAP-2 followed by opening of this epoxide by a histidine of the active site, a sequence that leads to irreversible inhibition of MetAP-2.

More recently, a new derivative of fumagillin has been synthesized: fumagalone, in which the epoxide group of fumagillin is replaced with an aldehyde group (Zhou G. et al. *J Med Chem.*, 2003, 46, 3452-3454). Fumagalone exhibits reversible inhibitory activity on the MetAP-2 enzyme in vitro, by reaction of the aldehyde group with histidine 231 of the MetAP-2 enzyme, forming an aminal. Fumagalone also displays inhibitory activity on the proliferation of endothelial cells in vivo.

This model suggests that analogues of fumagalone would be capable of interfering with the enzyme near the active site of MetAP-2. The present applicants used this enzyme for identifying novel fumagalone derivatives and so as to take advantage of better anti-angiogenic candidates for the topical and systemic treatment of disorders that may have a proliferative, inflammatory and/or immunosuppressive component, notably in the field of dermatology.

SUMMARY OF THE INVENTION

Novel compounds of formula (I) have now been developed, derived from fumagalone, by a method of synthesis which provides analogues that are difficult to prepare. This method of synthesis involves a stage of chiral deprotonation. The advantage of chiral deprotonation is that an enantiopure product is obtained from a compound having an element of planar symmetry. The action of a commercial chiral base on a prochiral cyclohexanone permits asymmetric deprotonation leading mainly to the formation of a chiral enolate. The enolate formed is at present asymmetric.

Thus the present invention features compounds having the following general formula (I):

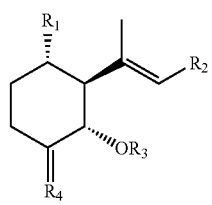

(I)

in which:
$R_1$ is a radical of structure (a) or of structure (b):

(a):

(b):

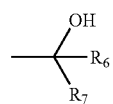

wherein $R_5$, $R_6$ and $R_7$ are as defined below;
$R_2$ is a lower alkyl radical having 1 to 5 carbon atoms;
$R_3$ is a lower alkyl radical having 1 to 5 carbon atoms;
$R_4$ is a radical of structure (c), bound by a single bond to the cyclohexane from which it depends:

(c)

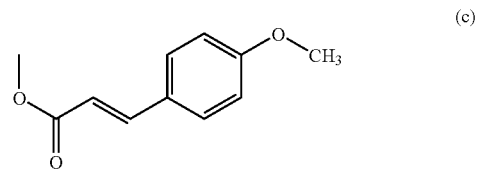

or $R_4$ is an oxygen atom bound by a double bond to the cyclohexane from which it depends;

$R_5$ is a hydrogen atom or a methyl radical or a trifluoromethyl radical; and $R_6$ and $R_7$ represent, independently of one another, a hydrogen atom or a trifluoromethyl radical.

The present invention also features the optical and geometric isomers, salts and mixtures of said compounds of formula (I).

DETAILED DESCRIPTION OF BEST MODE AND SPECIFIC/PREFERRED EMBODIMENTS OF THE INVENTION

According to the present invention, "lower alkyl radical" means an alkyl radical having from 1 to 5 carbon atoms, linear or branched, and in particular a methyl, ethyl, propyl, isopropyl, n-propyl, butyl, isobutyl, n-butyl, pentyl, isopentyl or n-pentyl radical.

According to the present invention, the more particularly preferred compounds of formula (I) are those for which at least one, and preferably all of the following conditions are satisfied:

$R_2$ is an isopentyl radical and more preferably a 3-methylbutyl radical;

$R_3$ is a methyl radical.

Figure 1:
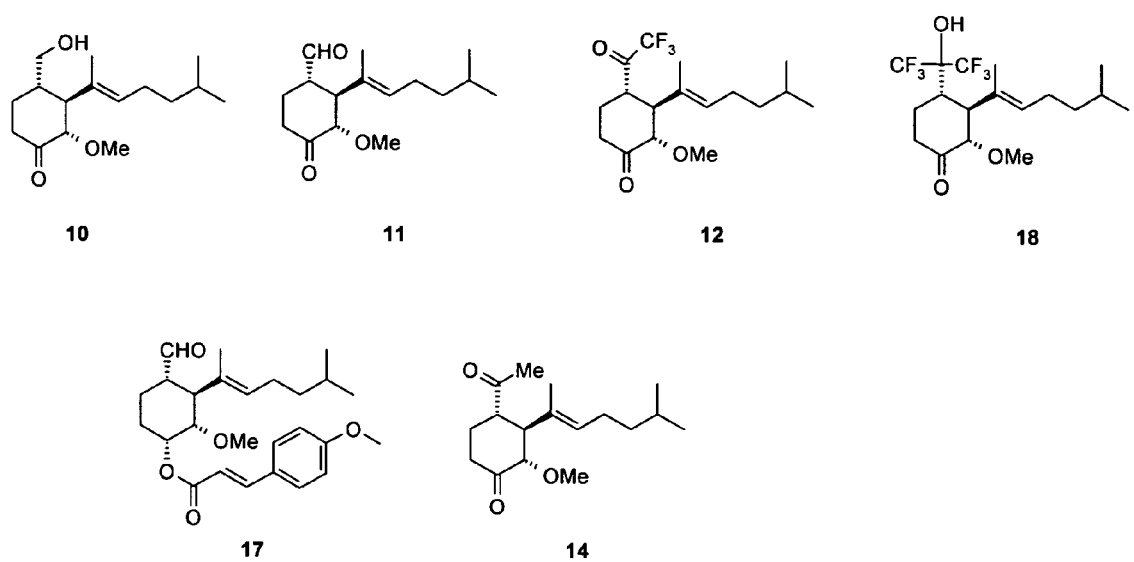
FIG. 1 illustrates several examples of the novel angiogenesis inhibiting compounds according to the present invention.

Among the compounds of formula (I) within the scope of the present invention, the following are particularly exemplary:

1: 2(S)-3(S)-4(S)-3-(1,5-Dimethyl-hex-1-enyl)-4-hydroxymethyl-2-methoxy-cyclohexanone;

2: 1(S)-2(S)-3(S)-2-(1,5-Dimethyl-hex-1-enyl)-3-methoxy-4-oxo-cyclohexanecarbaldehyde;

6: 2(S)-3(S)-4(S)-3-(1,5-Dimethyl-hex-1-enyl)-2-methoxy-4-(2,2,2-trifluoro-1-hydroxy-1-trifluoromethyl-ethyl)-cyclohexanone, which are shown in FIG. 1, and correspond respectively to the formulae of compounds 10, 11, 12, 14, 17 and 18.

Figure 2:
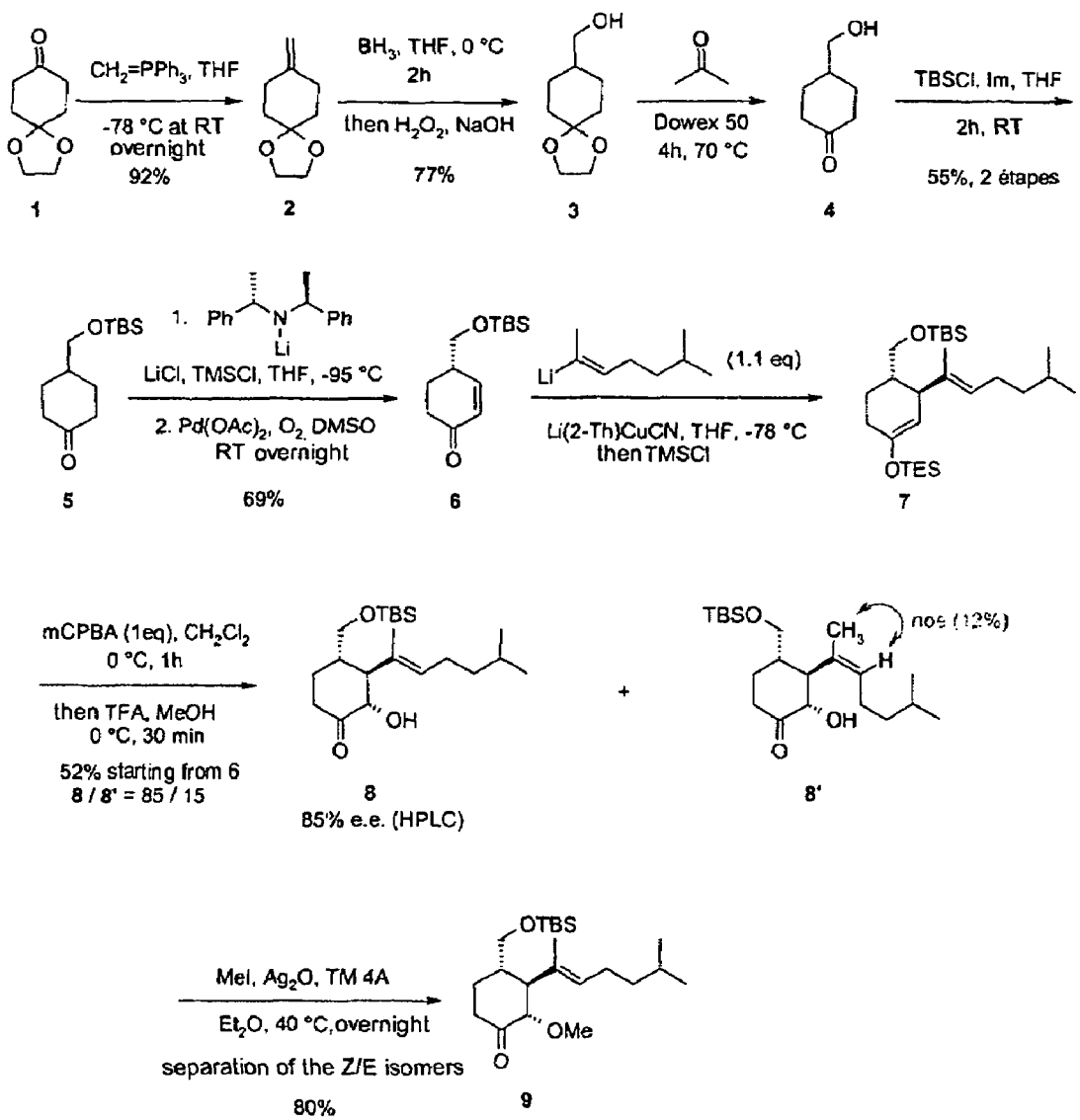
FIGS. 2, 3 and 4 illustrate a variey of reaction schemes for the ultimate synthesis of the novel fumagalone compounds of the invention.
Figure 3:
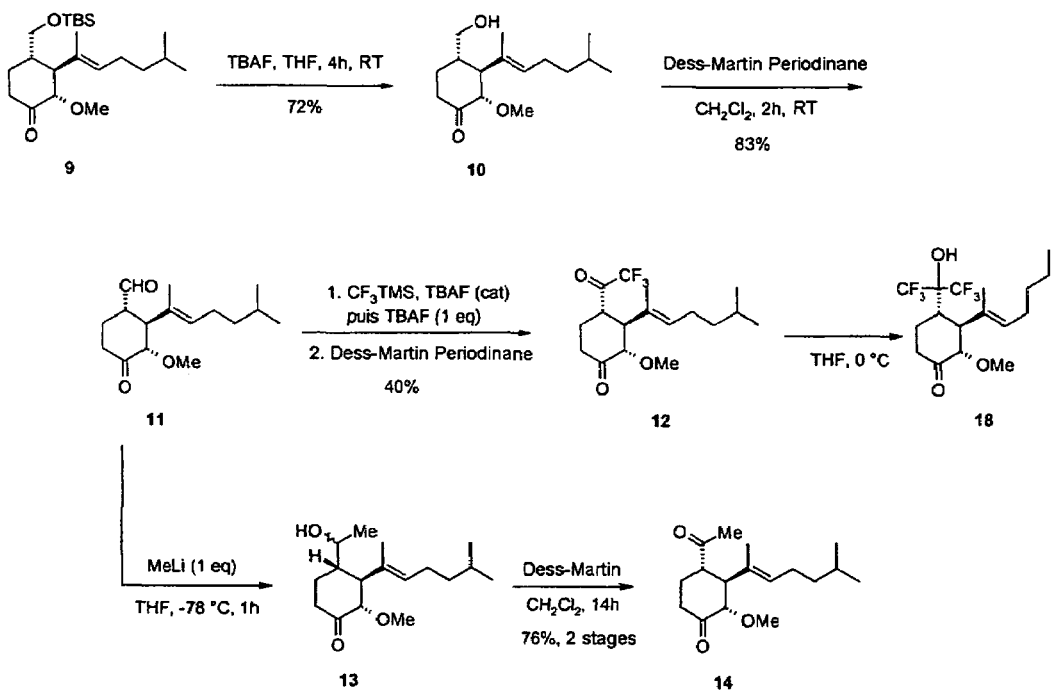
Figure 4:
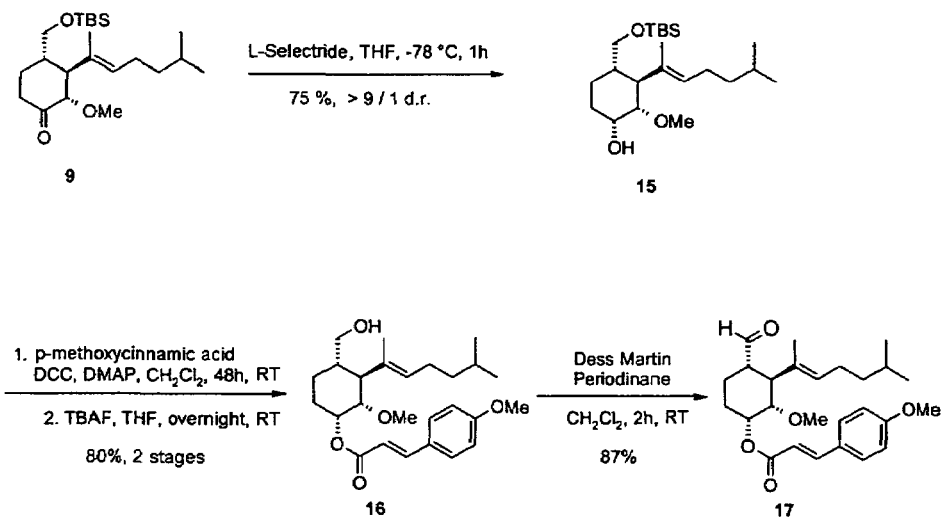

The present invention also features methods of preparation of the compounds of formula (I), or of possible isomers, optical and/or geometric, pure or in admixture, in all proportions, of said compounds of formula (I), of possible tautomeric forms, or of the salts of said compounds of formula (I), in particular according to the reaction schemes illustrated in FIGS. 2 to 4.

The methods of preparation of the compounds of formula (I) according to the invention are characterized notably by the synthesis of an intermediate 9 defined below, according to the method shown in FIG. 2.

The method of synthesis of the intermediate 9 is characterized by the following stages:

The monoacetal of commercially available cyclohexanedione 1: 1,4-dioxa-spiro[4.5]decan-8-one

1 is converted to compound 2: 8-methylene-1,4-dioxa-spiro[4.5]decane according to a Wittig reaction with for example triphenylmethylphosphonium ylide;

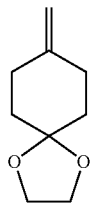

2 which is itself converted to alcohol 3: 1,4-dioxa-spiro[4.5]dec-8-yl-methanol according to a hydroboration reaction with for example borane followed by oxidative treatment;

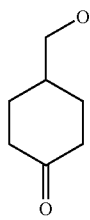

3 according to stages described in the literature: Nicolaou, K. C.; Magolda, R. L.; Claremon, D. A. *J. Am. Chem. Soc.*, 1980, 102, 1404-1409.

Compound 3 can be converted to ketone 4: 4-hydroxymethyl-cyclohexanone, by deprotection of the acetal in an acid environment, using a Dowex acid resin in form H⁺ for example.

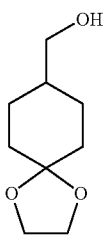

4

The primary alcohol of compound 4 can be protected by a silyl group using terbutyldimethylsilyl chloride for example, which leads to ketone 5: 4-(tert-butyl-dimethyl-silanyloxymethyl)-cyclohexanone

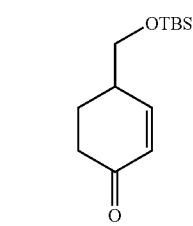

5

Asymmetric deprotonation of 5 gives, after oxidation of the intermediate silylated enol ether, cyclohexenone 6: 4(S)-4-(tert-butyl-dimethyl-silanyloxymethyl)-cyclohex-2-enone

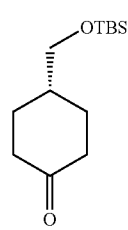

6 with an enantiomeric excess (e.e.) of 85% determined by chiral HPLC at the level of compound 8. This excess can also be determined on the basis of compound 6 after desilylation then esterification with Mosher esters, and NMR determination of the fluorine on the Mosher esters, in the manner shown in Example 7, it being understood that the values of 82% to 85% are similar and reflect good desymmetrization of the symmetric ketone 5.

1,4-Addition of a suitably selected cuprate to compound 6 gives, after treatment with triethyl silyl chloride, the enol ether 7: 3(R)-4(S)-3-(1,5-dimethyl-hex-1-enyl)-4-(tert-butyl-dimethyl-silanyloxymethyl)-1-triethylsilanyloxy-cyclohexene:

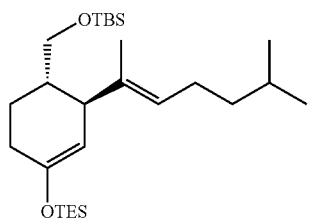

7

Oxidation of the silylated enol ether 7 (mCPBA) gives the α-hydroxyketone 8 (in form E): 2(S)-3(S)-4(S)-3-(1,5-dimethyl-hex-1-enyl)-2-hydroxy-4-(tert-butyl-dimethyl-silanyloxymethyl)-cyclohexanone

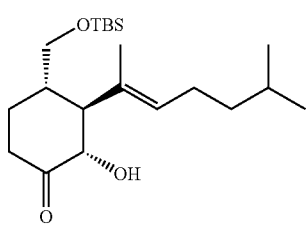

as well as, sometimes, in a mixture that cannot be separated at this stage, the Z isomer 8': 2(S)-3(S)-4(S)-3-(1,5-dimethyl-hex-1-enyl)-2-hydroxy-4-(tert-butyl-dimethyl-silanyloxymethyl)-cyclohexanone

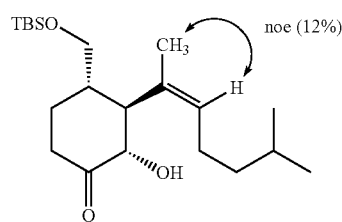

The pure compound 9: 2(S)-3(S)-4(S)-3-(1,5-dimethyl-hex-1-enyl)-4-(tert-butyl-dimethyl-silanyloxymethyl)-2-methoxy-cyclohexanone is obtained by methylation on compound 8, or, alternatively, depending on circumstances, on the mixed isomers 8 and 8', the isomers then easily being separated by techniques known to one skilled in this art.

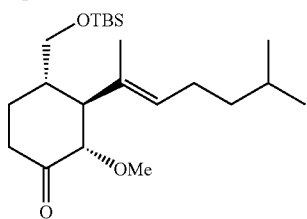

Thus, the present invention features a method of total synthesis of the fumagalone derivatives 10 to 14, 17 and 18 shown in FIG. 1, according to the reaction schemes shown in FIGS. 3 and 4.

According to the reaction scheme shown in FIG. 3, compound 9 gives compound 10: 2(S)-3(S)-4(S)-3-(1,5-dimethyl-hex-1-enyl)-4-hydroxymethyl-2-methoxy-cyclohexanone when treated with tetrabutyl ammonium fluoride for example:

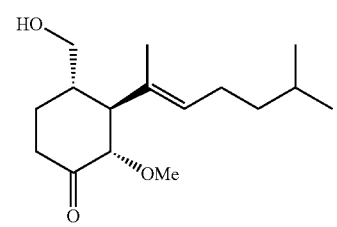

Oxidation of alcohol 10 by treatment with an oxidant, for example the Dess-Martin Periodinane, supplies aldehyde 11: 1(S)-2(S)-3(S)-2-(1,5-dimethyl-hex-1-enyl)-3-methoxy-4-oxo-cyclohexanecarbaldehyde:

11

Compound 11 reacts with the anion $CF_3^-$ to supply, after oxidation of the mixture of alcohols thus obtained, the trifluoromethyl ketone 12: 2(S)-3(S)-4(S)-3-(1,5-dimethyl-hex-1-enyl)-2-methoxy-4-(2,2,2-trifluoro-acetyl)-cyclohexanone:

12

By adding one equivalent of methyllithium to aldehyde 11 one can obtain the two alcohols 13: 2(S)-3(S)-4(S)-3-(1,5-dimethyl-hex-1-enyl)-2-hydroxy-4-(1-hydroxy-ethyl)-cyclohexanone:

13 which can be converted to one and the same ketone 14: 2(S)-3(S)-4(S)-4-acetyl-3-(1,5-dimethyl-hex-1-enyl)-2-methoxy-cyclohexanone:

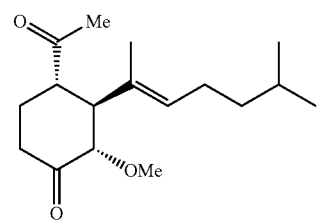

by the action of an oxidant, for example the Dess-Martin Periodinane.

According to the reaction scheme shown in FIG. 4, starting from 9, the selective reduction of the ketone function gives alcohol 15: 1(R)-2(S)-3(S)-4(S)-3-(1,5-dimethyl-hex-1-enyl)-4-(tert-butyl-dimethyl-silanyloxymethyl)-2-methoxy-cyclohexanol

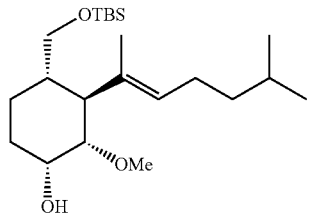

15 which is then esterified by means of para-methoxycinnamic acid to give, after desilylation, compound 16: 3-(1,5-dimethyl-hex-1-enyl)-4-(tert-butyl-dimethyl-silanyloxymethyl)-2-methoxy-cyclohexyl 1(R)-2(S)-3(S)-4(S)-[3-(4-methoxy-phenyl)]-acrylate:

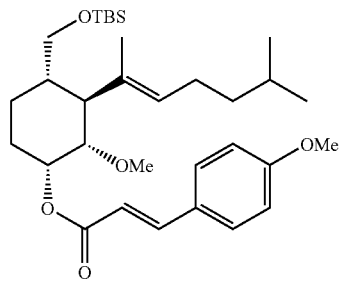

16 starting from which, oxidation of the primary alcohol finally gives aldehyde 17: 3-(1,5-dimethyl-hex-1-enyl)-4-formyl-2-methoxy-cyclohexyl 1(R)-2(S)-3(S)-4(S)-[3-(4-methoxy-phenyl)]-acrylate:

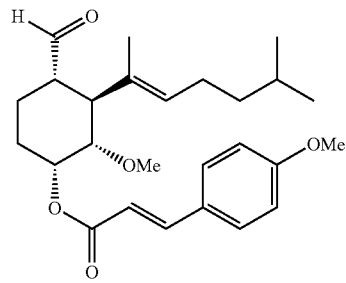

17

Compound 18: 2(S)-3(S)-4(S)-3-(1,5-dimethyl-hex-1-enyl)-2-methoxy-4-(2,2,2-trifluoro-1-hydroxy-1-trifluoromethyl-ethyl)-cyclohexanone:

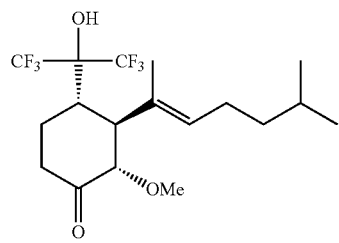

18 is obtained by addition of CF$_3$TMS to compound 12, defined previously.

The compounds according to the invention find application in dermatology, in particular in the topical and systemic treatment of conditions associated with a disorder of angiogenesis, and they also find applications outside of dermatology.

The compounds of general formula (I) display anti-angiogenic biological properties. This activity can be demonstrated in vitro by a method using a commonly accepted biological target of fumagillin and its analogues, a methionine aminopeptidase (MetAP-2) identified by Griffith et al. (Griffith, E. C. et al. Chem. Biol. 1997, 4(6), 461-471). The inhibitory activity of various derivatives of fumagillin against this enzyme displays good correlation with the anti-angiogenic effect.

As an example, the biological activity of the compounds is evaluated by measuring their inhibitory activity on methionine aminopeptidase MetAP-2 (Li, X., Chang, Y-H. Biochem. Biophys. Res. Comm., 1996, 227, 152).

Biological activity is characterized, in this system, by determining the concentration of compound required as inhibitor for inhibiting 50% of the enzyme activity (IC$_{50}$).

The present invention also features pharmaceutical compositions comprising at least one compound of formula (I) as defined above formulated into a pharmaceutically acceptable carrier.

The present invention therefore also features such pharmaceutical compositions as medicinal products notably suited for the treatment of the aforementioned disorders.

The compositions according to the invention can be administered in a regime or regimen via the oral, parenteral, topical or ocular route.

For the oral route, the pharmaceutical compositions can be in the form of tablets, capsules, sugar-coated pills, syrups, suspensions, solutions, powders, granules, emulsions, suspensions of microspheres or nanospheres or lipid or polymeric vesicles providing controlled release.

For the parenteral route, the compositions can be in the form of solutions or suspensions for infusion or for injection.

The compounds according to the invention are generally administered at a daily dose from about 0.001 mg/kg to 500 mg/kg and preferably from about 0.01 mg/kg to 50 mg/kg of body weight in 1 to 3 doses.

For the topical route, the pharmaceutical compositions based on compounds according to the invention are intended for the treatment of the skin and of the mucosae and are in the form of unguents, creams, milks, ointments, powders, impregnated tampons, solutions, gels, sprays, lotions or suspensions. They can also be in the form of suspensions of microspheres or nanospheres or lipid or polymeric vesicles or in the form of polymeric patches and hydrogels providing controlled release. These compositions for topical application can either be in anhydrous form, or in aqueous form, depending on the clinical indication.

For the ocular route, they are mainly eye washes.

The pharmaceutical compositions of the present invention, notably for the topical or ocular route, contain at least one compound of formula (I) as defined above at a concentration preferably from 0.0001% and 20% to more preferably from 0.001% and 5% relative to the total weight of the composition.

The present invention also features the pharmaceutical compositions as defined above, as medicinal products.

The pharmaceutical compositions of the present invention are particularly suitable for the treatment of conditions associated with a disorder of angiogenesis, such as rosacea.

The compounds of formula (I) according to the invention also find application in the cosmetic field, in particular for care of the skin or of the scalp and notably for the treatment of skin that is prone to acne, for regrowth of hair, as hair restorer, to combat greasy appearance of the skin or of the hair, for protection against the harmful effects of the sun or in the treatment of physiologically dry skin, and for preventing and/or combating photo-induced or chronological aging.

The present invention therefore also features cosmetic compositions containing, in a cosmetically acceptable carrier, at least one compound of formula (I) as defined above.

These cosmetic compositions can notably be in the form of a cream, a milk, a lotion, a gel, suspensions of microspheres or nanospheres or lipid or polymeric vesicles, a soap or a shampoo.

The concentration of compound of formula (I) in the cosmetic compositions can be from 0.0001 and 3 wt. % relative to the total weight of the composition.

The compounds according to the invention can also be used in cosmetic compositions for body and hair hygiene.

In the pharmaceutical and cosmetic fields, the compounds according to the invention can be employed advantageously in combination with retinoids, with corticosteroids or oestrogens, together with free-radical scavengers, with α-hydroxy or α-keto acids or their derivatives, with derivatives of salicylic acid, or with blockers of ion channels such as potassium channels, or—more particularly for pharmaceutical compositions—in combination with medicinal active agents that are known to interact with the immune system.

The pharmaceutical and cosmetic compositions according to the invention can, in addition, contain inert or even pharmacodynamically or cosmetically active additives or combinations of these additives, and notably:

wetting agents;
depigmenting agents;
emollients;
moisturizers;
antibiotics;
anti-fungal agents;
agents promoting hair regrowth;
non-steroidal anti-inflammatory agents;
carotenoids.

The pharmaceutical and cosmetic compositions according to the invention can also contain agents for improving taste, preservatives, stabilizers, moisture content regulators, pH regulators, agents for modifying osmotic pressure, emulsifiers, UV-A and UV-B filters, and antioxidants.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Synthesis of 2(S)-3(S)-4(S)-3-(1,5-dimethyl-hex-1-enyl)-4-hydroxymethyl-2-methoxy-cyclohexanone (Compound 10 in FIG. 1)

a—Preparation of Olefin 2:

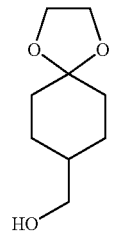

Add BuLi (13.2 mL, 1.6M in hexane, 21.15 mmol, 1.1 eq) to a solution of methyl triphenylphosphonium bromide (7.89 g, 22.11 mmol, 1.15 eq) in THF (50 mL) at −78° C. Stir this suspension for 10 min at −78° C., then 30 min at 0° C. Then cool the orange solution obtained to −78° C., and add a solution of the monoethylene ketal of 1,4-cyclohexanedione (3 g, 19.23 mmol) in THF (10 mL). Stir the reaction mixture overnight at room temperature (RT), then filter on Celite. Rinse the solid with pentane. After evaporating the solvents, chromatograph the residue on silica gel (eluent CyH/AcOEt 95/5). 2.7 g (92%) of olefin 2 is thus obtained (colorless oil).

b—Preparation of Alcohol 3:

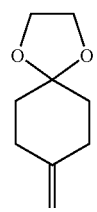

Treat alkene 2 (2 g, 13 mmol) in solution in THF (30 mL) with $BH_3$ (1M in THF, 13 mL, 13 mmol, 3 eq) at 0° C. Stir the reaction mixture for 2 h at this temperature, then hydrolyze by adding MeOH (5 mL). Slowly add NaOH (3N, 15 mL) then $H_2O_2$ (30%, 6 mL) to this solution, keeping the temperature below 40° C. Stir the mixture obtained for 1 h at RT, then extract with AcOEt. Wash the organic phase with $Na_2S_2O_3$ (saturated aqueous solution), dry over $MgSO_4$, and evaporate the solvents at reduced pressure. 1.7 g of alcohol 3 is obtained (77%), without the need for further purification.

$^1$H NMR (400 MHz, $CDCl_3$): 3.95 (m, 4H, O—$CH_2$—$CH_2$—O), 3.49 (d, J=6.4, 2H, $CH_2OH$), 1.77 (m, 4H), 1.58-1.50 (m, 3H), 1.32-1.22 (m, 2H). Ref for 2 and 3: Nicolaou, K. C.; Magolda, R. L.; Claremon, D. A. *J. Am. Chem. Soc.*, 1980, 102, 1404-1409.

c—Preparation of Compound 5:

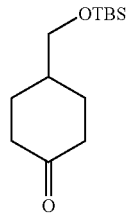

Heat alcohol 3 (1 g, 5.88 mmol) in solution in acetone (100 mL) for 4 h at 70° C. in the presence of acid resin DOWEX 50W (300 mg). Then filter the solution, neutralize with $Et_3N$ then evaporate the solvent at reduced pressure. Dissolve the residue obtained in THF (10 mL), then add TBSCl (640 mg, 4.3 mmol) and imidazole (540 mg, 7.8 mmol), plus a catalytic amount of DMF. Stir the mixture obtained for 2 h at RT, then stop the reaction by adding a saturated aqueous solution of $NH_4Cl$, and extract with cyclohexane (CyH). After drying the organic phases and evaporating the solvents, purify the residue obtained on silica gel (eluent CyH/AcOEt 95/5). 700 mg (55%) of compound 5 is obtained in the form of a colorless oil.

Anal. calcd for $C_{13}H_{26}O_2Si$, C, 64.41; H, 10.81. found C, 64.12; H, 10.92.

$^{1}$H NMR (400 MHz, CDCl$_3$): 3.50 (d, J=6.3, 2H, CH$_2$OTBS), 2.45-2.25 (m, 4H), 2.05 (m, 2H), 1.90 (m, 1H), 1.42 (m, 2H), 0.89 (s, 9H, $^t$Bu), 0.04 (s, 6H, (Me)$_2$Si).

$^{13}$C NMR (100 MHz, CDCl$_3$): 212.2, 67.0, 40.5, 38.7, 29.2, 25.9, 18.3, −5.4 d—Preparation of Cyclohexenone 6:

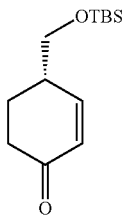

Add BuLi (11.98 mL, 1.6M in hexane, 19.16 mmol, 2.3 eq) to a suspension of (+)-bis[(R)-1-phenylethyl]amine hydrochloride (2.5 g, 9.6 mmol, 1.15 eq) in 30 mL of THF at −78° C. Stir the mixture for 10 min at −78° C., and 15 min at 0° C., then cool to −100° C. (MeOH/N$_2$). Then add Me$_3$SiCl (4.2 mL, 33 mmol, 4 eq), followed by ketone 5 (2 g, 8.33 mmol) in solution in 10 mL of THF. Stir the solution for 2 h from −100° C. and −95° C. Then add 15 mL of Et$_3$N, followed by a saturated solution of NaHCO$_3$. After extraction (AcOEt), dry the organic phases over MgSO$_4$ and evaporate to give a brown oil; filter this quickly on silica gel (CyH/AcOEt/Et$_3$N 97.5/2.5/1). 2 g of a colorless oil is obtained.

Dissolve this oil in DMSO (100 mL) and treat with Pd(OAc)$_2$ (180 mg, 0.8 mmol, 10%), then stir the solution obtained vigorously overnight under an atmosphere of O$_2$. After hydrolysis at 0° C. with NH$_4$Cl, extraction with Et$_2$O and evaporation of the organic phases, 1.37 g (69%) of enone 6 is obtained in the form of a brown oil, which can be purified on a preparative silica plate to give an analytically-pure colorless oil.

[α]$_D^{20}$=−93° (CHCl$_3$, C=1.5)

$^{1}$H NMR (400 MHz, CDCl$_3$): 6.93 (dq, J=10.2, 2.0, 1H, C=O—CH=CH), 6.00 (dd, J=10.2, 2.2, 1H, C=O—CH=CH), 3.60 (m, 2H, CH$_2$—OTBS), 2.58 (m, 1H, CH—CH$_2$OTBS), 2.52 (dt, J=16.6, 4.9, 1H, C=O—CHH), 2.36 (ddd, J=16.6, 12.8, 4.9, 1H, C=O—CHH), 2.07 (dq, J=12.8, 4.9, 1H, C=O—CH$_2$—CHH), 1.74 (tdd, J=12.8, 9.9, 4.5, 1H, C=O—CH$_2$—CHH), 0.86 (s, 9H, $^t$Bu), 0.03 (s, 6H, (Me)$_2$Si).

$^{13}$C NMR (100 MHz, CDCl$_3$): 199.8, 151.9, 129.9, 65.5, 39.2, 36.7, 25.9, 25.5, 18.3, −5.4.

Anal. calcd for C$_{13}$H$_{24}$O$_2$Si: C, 64.95; H, 10.06. found: C, 64.92; H, 10.03.

e—Preparation of Compound 8:

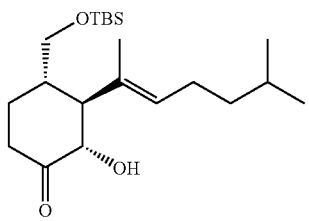

Add $^t$BuLi (9.1 mL, 13.65 mmol, 1.5 M in pentane, 2.5 eq) to a solution of (E)-2-bromo-6-methyl-hept-2-ene, which can be obtained for example according to the method described in Example 8b, (1.45 g, 7.6 mmol, 1.4 eq) in THF (40 mL) at −78° C. After 20 min, add a solution of lithium 2-thienylcyanocuprate (Li(2-th)CuCN) (30.4 mL, 0.25 M in THF, 7.6 mmol, 1.4 eq) via a tube, then keep the solution obtained at −78° C. for 20 min. Then add a solution of cyclohexenone 6 (1.3 g, 5.46 mmol) in THF (10 mL) via a tube to the solution previously obtained, and stir the mixture obtained for 30 min at −78° C. Then add TMSCl (1 mL, 8.2 mmol, 1.5 eq), and after 30 min, stop the reaction by adding, in succession, Et$_3$N (2 mL) then saturated aqueous solution of NaHCO$_3$. After extraction (Et$_2$O), drying (MgSO$_4$) and evaporation of the solvents, the silylated enol ether is obtained as a brown oil (2.3 g). Dissolve this oil in CH$_2$Cl$_2$ (50 mL), cool the mixture to 0° C. and add KHCO$_3$ (2.5 g, 25 mmol, 5 eq) and then mCPBA (~70%, 1.3 g, 5.46 mmol, 1 eq). After 1 h, filter the mixture, then treat with a solution of Na$_2$S$_2$O$_3$. After extraction (CH$_2$Cl$_2$), drying of the organic phases (MgSO$_4$) and evaporation of the solvents under reduced pressure, dissolve the residue obtained in a mixture MeOH/THF 10/1 (55 mL) and cool to 0° C. Add trifluoroacetic acid (TFA) (38 µL, 0.5 mmol, 0.1 eq) and stir the mixture for 30 min. Stop the reaction by adding saturated aqueous solution of NaHCO$_3$, then extract with Et$_2$O. After drying the organic phases and evaporating the solvents at reduced pressure, chromatograph the residue obtained on silica gel (230-400 mesh, eluent CyH/AcOEt 9/1). Alcohol 8 is obtained in the form of a colorless oil (1.04 g, 52%). e.e.=85% (Chiral HPLC, Chiralpack AD).

$^{1}$H NMR (400 MHz, CDCl$_3$): 5.25 (t, J=6.6, C=CH), 4.12 (d, J=11.2, 1H, CHOH), 3.54 (dd, J=10.1, 3.3, 1H, CHH—OTBS), 3.44 (brs, 1H, OH), 3.28 (dd, J=10.1, 6.8, 1H, CHH—OTBS), 2.59 (ddd, J=13.8, 4.5, 2.5, 1H, CHH—CH$_2$—C=O), 2.43 (tdd, J=14.1, 6.3, 1.1, 1H, CHH—C=O), 2.25 (dm, J=14.1, 1H, CHH—C=O), 2.12-2.01 (m, 3H, CH—CH—OH & C=CH—CH$_2$), 1.95 (m, 1H, CH—CH$_2$OTBS), 1.66 (s, 3H, Me), 1.59-1.47 (m, 2H, CHH—CH$_2$—C=O & CH(Me)$_2$), 1.23 (q, J=7.4, 2H, CH$_2$—CH(Me)$_2$), 0.88 (d, J=7.4, 6H, (Me)$_2$—CH), 0.87 (s, 9H, $^t$Bu), 0.00 (s, 6H, (Me)$_2$Si).

$^{13}$C NMR (100 MHz, CDCl$_3$): 210.9, 131.1, 130.2, 75.5, 64.5, 58.7, 39.4, 38.8, 38.1, 29.3, 27.5, 25.9, 25.6, 22.6, 22.3, 18.2, 11.7, −5.5, −5.6.

f—Preparation of Compound 9:

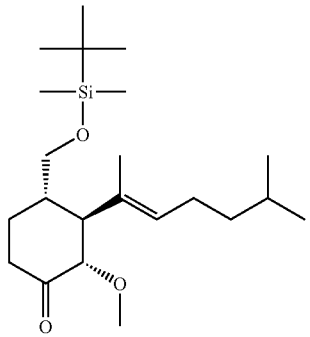

Add methyl iodide (3 mL) to a suspension of silver oxide (3.15 g, 13.5 mmol, 5.0 eq) and of molecular sieve 4 Å (800 mg) in diethyl ether (10 mL), in the presence of alcohol 8 (1 g, 2.7 mmol). Stir the suspension for 3 hours at 40° C. Filter the reaction mixture on Celite and then evaporate the solvents. Chromatograph the oil residue on silica gel (CyH/AcOEt 9/1). Compound 9 (1 g, 96%) is obtained in the form of a colorless oil.

[α]$_D^{20}$=4.0° (CHCl$_3$, C=1.7)

$^{1}$H NMR (400 MHz, CDCl$_3$): 5.21 (t, J=6.8, C=CH), 4.12 (d, J=11.4, CH—OMe), 3.54 (dd, J=9.8, 3.1, 1H, CHH—OTBS), 3.39 (s, 3H, OMe), 3.29 (dd, J=9.8, 6.8, 1H, CHH—OTBS), 2.45 (ddd, J=13.4, 4.8, 3.0, 1H, CHH—C=O), 2.42-2.32 (m, 1H, CHH—C=O), 2.25 (t, J=11.4, 1H, CH—C(Me)

=C), 2.18 (m, 1H, CHH—CH₂—C=O), 2.04 (m, 2H, C=CH—CH₂), 1.92 (m, 1H, CH—CH₂—OTBS), 1.61 (s, 3H, Me), 1.60-1.45 (m, 3H, CH₂—CH(Me)₂ & CHH—CH₂—C=O), 1.23 (m, 2H, CH₂—CH(Me)₂), 0.88 (d, J=6.8, 6H, (Me)₂—CH), 0.86 (s, 9H, ᵗBu), 0.00 (s, 6H, (Me)₂Si).

¹³C NMR (100 MHz, CDCl₃): 209.6, 131.2, 129.5, 84.9, 64.5, 58.9, 56.5, 40.4, 39.7, 38.7, 29.4, 27.4, 25.9, 25.6, 22.6, 22.5, 18.3, 12.0, −5.4, −5.5.

g—Synthesis of Compound 10:

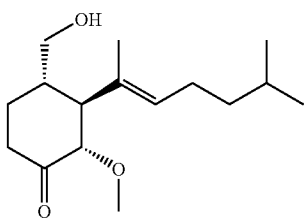

Dissolve compound 9 (765 mg, 2.0 mmol) in THF (50 mL), then treat with tetrabutylammonium fluoride TBAF (2.2 mL, 2.2 mmol, 1.1 eq). Stir this solution for 4 h at RT, then hydrolyze by adding a saturated solution of NH₄Cl. After extraction with ethyl acetate, combine the organic phases, dry over anhydrous magnesium sulfate and evaporate the solvents. The residue obtained is chromatographed on silica gel (CyH/AcOEt: 9/1→8/2). Alcohol 10 is obtained in the form of a colorless oil (450 mg, 84%).

[α]$_D^{20}$=14.9° (CHCl₃, C=1.75)

Anal. calcd for C₁₆H₂₈O₃: C, 71.60; H, 10.52. found: C, 71.18; H, 10.67.

HRMS (FAB) m/z found 268.2043, calcd for C₁₆H₂₈O₃ m/z 268.2038.

¹H NMR (400 MHz, CDCl₃): 5.28 (t, J=7.0, C=CH), 3.76 (dd, J=11.5, 0.8, 1H, CHOMe), 3.59 (dd, J=11.2, 4.4, 1H, CHH—OH), 3.42 (dd, J=11.2, 6.0, 1H, CHH—OH), 3.40 (s, 3H, OMe), 2.48 (ddd, J=13.7, 5.0, 3.0, 1H, CHH—CH₂¹³C=O), 2.41 (tdd, J=13.7, 6.0, 1.0, 1H, CHH—C=O), 2.23 (t, J=11.5, 1H, CH—C(Me)=C), 2.14 (m, 1H, CHH—C=O), 2.06-2.02 (m, 3 h, C=CH—CH₂ & CHH—CH₂—C=O), 1.65 (s, 3H, Me), 1.55 (m, 3H, CH₂—CH(Me)₂ & OH & CH—CH₂OH), 1.23 (m, 2H, CH₂—CH(Me)₂), 0.87 (d, J=7.0, 6H, (Me)₂—CH).

¹³C NMR (100 MHz, CDCl₃): 209.0, 132.2, 129.9, 84.6, 65.2, 58.9, 57.5, 40.6, 39.6, 38.6, 29.2, 27.6, 25.7, 22.5, 11.9.

EXAMPLE 2

Synthesis of 1(S)-2(S)-3(S)-2-(1,5-dimethyl-hex-1-enyl)-3-methoxy-4-oxo-cyclohexanecarbaldehyde (Compound 11 in FIG. 1)

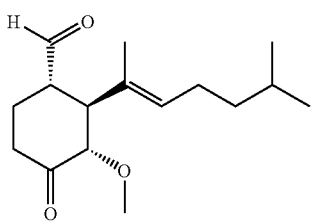

Treat alcohol 10 (430 mg, 1.67 mmol), in solution in CH₂Cl₂ (10 mL), with the Dess-Martin Periodinane (4.2 mL, 15% solution in CH₂Cl₂, 1.2 eq) in the presence of H₂O (20 μL). Stir the solution for 2 h at RT, then stop the reaction by adding a 1/1 mixture NaHCO₃/Na₂S₂O₃ as saturated aqueous solutions. Stir this mixture vigorously for 1 h at RT, then extract with CH₂Cl₂. Then purify the residue on silica gel (eluent CyH/AcOEt: 9/1→8/2). Aldehyde 11 is obtained in the form of a colorless oil (355 mg, 83%).

[α]$_D^{20}$=+3.3° (CHCl₃, C=1.0)

HRMS (FAB) m/z found 266.1885. calcd for C₁₆H₂₆O₃ m/z: 266.1882.

¹H NMR (400 MHz, CDCl₃): 9.47 (d, J=2.8, 1H, CHO), 5.31 (t, J=7.0, C=CH), 3.77 (d, J=9.6, 1H, CH—OMe), 3.40 (s, 3H, OMe), 2.65 (tt, J=10.8, 3.4, 1H, CH—CHO), 2.70 (t, J=10.8, 1H, CH—C(Me)=CH), 2.57 (dt, J=13.3, 4.3, 1H, CHH—C=O), 2.41 (td, J=13.3, 5.8, 1H, CHH—C=O), 2.09 (m, 1H, CHH—CH₂—C=O), 2.02 (q, J=7.0, 2H, C(Me)=CH—CH₂), 1.81 (tdd, J=13.3, 10.8, 4.3, 1H, CHH—CH₂—C=O), 1.67 (s, 3H, Me), 1.51 (hept, J=6.7, 1H, CH₂—CH(Me)₂), 1.20 (m, 2H, CH₂—CH(Me)₂), 0.86 (d, J=6.7, 6H, (Me)₂—CH).

¹³C NMR (100 MHz, CDCl₃): 207.6, 201.5, 130.9, 130.5, 84.4, 58.9, 54.9, 50.4, 38.6, 38.4, 27.5, 25.7, 25.4, 22.4, 12.9.

EXAMPLE 3

Synthesis of 2(S)-3(S)-4(S)-3-(1,5-dimethyl-hex-1-enyl)-2-methoxy-4-(2,2,2-trifluoro-acetyl)-cyclohexanone (Compound 12 in FIG. 1)

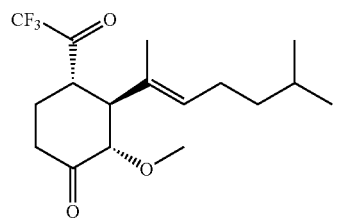

Treat aldehyde 11 (50 mg, 188 μmol), in solution in THF (1 mL), with CF₃SiMe₃ (30 μL, 197 μmol, 1.05 eq) and TBAF (10 μL, 0.05 eq) at 0° C. After 1 h at this temperature, hydrolyze the mixture by adding a saturated solution of NH₄Cl. After extraction with ethyl acetate, combine the organic phases, dry over anhydrous magnesium sulfate and evaporate the solvents. Dissolve the residue obtained in THF (1 mL), then add TBAF (200 μL, 1 eq). After 30 min, hydrolyze the reaction mixture by adding a saturated solution of NH₄Cl. After extraction with ethyl acetate, combine the organic phases, dry over anhydrous magnesium sulfate and evaporate the solvents. Dissolve the residue obtained in CH₂Cl₂ (1 mL), then add the Dess-Martin Periodinane (1.6 mL, 770 μmol, 4 eq). Stir the mixture overnight at 0° C., then hydrolyze by adding a saturated solution of NaHCO₃ plus a saturated solution of Na₂S₂O₃. Stir the mixture obtained for 1 h at 0° C., then extract with CH₂Cl₂. Combine the organic phases, dry over anhydrous magnesium sulfate, then evaporate the solvents. Purify the residue obtained by preparative TLC (CyH/Et₂O:9/1). Ketone 12 is obtained in the form of a colorless oil (25 mg, 40%).

[α]$_D^{20}$=−8° (CHCl₃, C=0.5)

HRMS (FAB) m/z found 334.1755. calcd for C₁₇H₂₅O₃F₃ m/z: 334.1756.

¹H NMR (400 MHz, CDCl₃): 5.22 (t, J=6.3, 1H, C=CH), 3.80 (d, J=11.6, 1H, CH—OMe), 3.46 (td, J=11.6, 3.5, 1H,

CH—CO(CF$_3$)), 3.42 (s, 3H, OMe), 2.82 (t, J=11.6, 1H, CH—C(Me)=CH), 2.57 (ddd, J=13.7, 4.5, 3.0, 1H, CHH—CO), 2.47 (td, J=13.7, 5.8, 1H, CHH—CO), 2.21 (m, 1H, C=O—CH$_2$—CHH), 1.97 (q, J=7.6, 2H, CH$_2$—CH=C), 1.81 (tdd, J=13.3, 12.1, 4.5, 1H, C=O—CH$_2$—CHH), 1.64 (s, 3H, Me), 1.47 (hept, J=6.5, 1H, CH(Me)$_2$), 1.15 (m, 2H, CH$_2$—CH(Me)$_2$), 0.85 & 0.84 (2d, J=6.5, 6H, (Me)$_2$).

$^{13}$C NMR (100 MHz, CDCl$_3$): 206.4, 191.3 (q, $^2J_{C-F}$=35.3 Hz), 131.6, 130.6, 115.4 (q, $^1J_{C-F}$=29.03 Hz), 84.5, 59.1, 55.3, 46.5, 39.1, 38.1, 28.8, 27.4, 25.6, 22.4, 22.3, 12.9.

$^{19}$F NMR (376 MHz, CDCl$_3$): −74.9 (s).

EXAMPLE 4

Synthesis of 2(S)-3(S)-4(S)-4-acetyl-3-(1,5-dimethyl-hex-1-enyl)-2-methoxy-cyclohexanone (Compound 14 in FIG. 1)

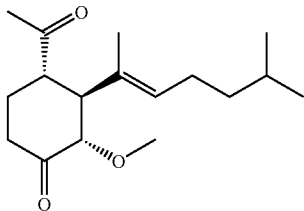

A −78° C., add MeLi (64 µL, 1.4 M in Et$_2$O, 90 µmol, 1.2 eq) to a solution of aldehyde 11 (20 mg, 75 µmol) in THF (2 mL). Stir the solution for 30 min at this temperature, then stop the reaction by adding a saturated aqueous solution of NH$_4$Cl. After extraction (AcOEt) and evaporation of the organic solvents at reduced pressure, dissolve the residue obtained in CH$_2$Cl$_2$ then treat with a solution of the Dess-Martin Periodinane (282 µL, 15% solution in CH$_2$Cl$_2$, 112 µmol, 1.4 eq) then stir the solution obtained overnight at RT. Hydrolyze the reaction mixture by adding saturated solutions of NaHCO$_3$ (1 mL) and Na$_2$S$_2$O$_3$ (1 mL). The mixture obtained is stirred vigorously for 30 min, then extracted (CH$_2$Cl$_2$). After evaporation of the solvents at reduced pressure, purify the residue obtained by preparative TLC (eluent CyH/AcOEt 9/1). Ketone 14 is obtained in the form of a colorless oil (16 mg, 76%).

[α]$_D^{20}$=−9.4° (CHCl$_3$, C=0.8)

$^1$H NMR (400 MHz, CDCl$_3$) 5.24 (t, J=7.0, 1H, (Me)C=CH), 3.74 (d, J=11.6, 1H, CH—OMe), 3.40 (s, 3H, OMe), 3.00 (td, J=11.6, 3.6, 1H, CH—C=O(Me)), 2.61 (t, J=11.6, 1H, CH—C(Me)=CH), 2.53 (ddd, J=13.6, 4.5, 3.0, 1H, CHeqH—C=O), 2.41 (td, J=13.6, 5.8, 1H, CHHax-C=O), 2.07 (s, 3H, Me—C=O), 2.05 (m, 1H, CHH—CH$_2$—C=O), 2.00 (q, J=7.0, C=CH—CH$_2$), 1.79 (qd, J=13.6, 4.5, CHH—CH$_2$—C=O), 1.66 (s, 3H, Me—C=CH), 1.51 (hept, J=6.6, 1H, CH(Me)$_2$), 1.18 (m, 2H, CH$_2$—CH(Me)$_2$), 0.86 & 0.85 (2 d, J=6.7, 6H, CH(Me)$_2$).

$^{13}$C NMR (100 MHz, CDCl$_3$): 208.6, 207.6, 131.3, 130.4, 84.9, 59.0, 56.4, 53.4, 39.4, 38.5, 29.0, 28.2, 27.5, 25.7, 22.5, 12.8.

EXAMPLE 5

Synthesis of 1(R)-2(S)-3(S)-4(S)-3-(4-methoxy-phenyl)-acrylic acid 3-(1,5-dimethyl-hex-1-enyl)-4-formyl-2-methoxy-cyclohexyl ester (Compound 17 in FIG. 1)

a—Preparation of Compound 15:

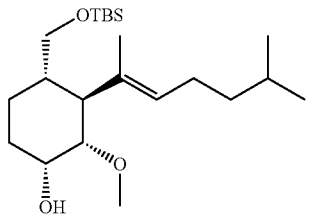

Treat ketone 9 (85 mg, 222 µmol), in solution in THF (1.5 mL), with L-Selectride (1M in THF, 0.35 mL, 1.5 eq) at −78° C. After 1 h at this temperature, stop the reaction by adding a solution of NH$_4$Cl, then extract with AcOEt. After drying (MgSO$_4$) and evaporation of the solvents at reduced pressure, purify the residue by preparative TLC (eluent CyH/AcOEt 85/15). Alcohol 15 is obtained in the form of a colorless oil (60 mg, 70%).

[α]$_D^{20}$=+15° (CHCl$_3$, C=0.8)

$^1$H NMR (400 MHz, CDCl$_3$): 5.19 (t, J=7.5, 1H, C=CH), 4.20 (br s, 1H, CH—OH), 3.49 (dd, J=10.0, 2.5, 1H, CHH—OTBS), 3.34 (s, 3H, OMe), 3.19 (dd, J=10.0, 7.4, 1H, CHH—OTBS), 3.08 (dd, J=10.7, 2.7, 1H, CH—OMe), 2.16 (t, J=10.7, 1H, CH—C(Me)=CH), 2.15 (br s, 1H, OH), 2.10-2.00 (m, 3H, C=CH—CH$_2$ & CHH—CHOH), 1.68 (m, 1H, CHH—CHOH), 1.56 (s, 3H, CH$_3$—C=CH), 1.55 (hept, J=7.0, 1H, CH(Me)$_2$), 1.45-1.35 (m, 3H, CH—CH$_2$OTBS & CH$_2$—CH(CH$_2$OTBS)), 1.24 (q, J=7.0, 2H, CH$_2$—CH(Me)$_2$), 0.88 & 0.87 (2d, J=7.0, 6H, CH(Me)$_2$), 0.87 (s, 9H, $^t$Bu), 0.00 (s, 6H, (Me)$_2$Si).

$^{13}$C NMR (100 MHz, CDCl$_3$): 132.6, 128.3, 82.4, 65.8, 64.9, 57.1, 48.7, 40.7, 38.9, 29.1, 27.5, 26.0, 25.6, 22.6, 22.4, 18.4, −5.3, −5.4.

Anal. calcd for C$_{22}$H$_{44}$O$_3$Si: C, 68.69; H, 11.53. found C, 68.83; H, 11.74.

b—Preparation of Compound 16:

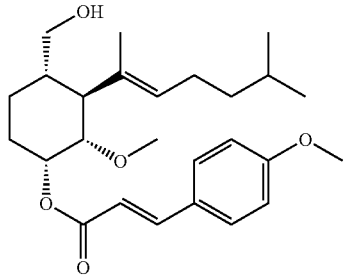

Add p-methoxycinnamic acid (104 mg, 0.58 mmol, 5 eq), immediately followed by DMAP (71 mg, 0.58 mmol, 5 eq) and DCC (120 mg, 0.58 mmol, 5 eq), to a solution of the alcohol (45 mg, 0.117 mmol, 1.0 eq) in dichloromethane (3 mL). Stir the reaction mixture for 48 h at RT. Evaporate the solvents and filter the residue on a silica column (eluent: Cy/AcOEt 9/1). Dissolve the impure oil obtained in THF (2 mL) and treat with TBAF (0.15 mL, 1.3 eq). Stir the mixture overnight, then stop the reaction with NH₄Cl and extract with AcOEt. Dry the organic phases (MgSO₄) and evaporate the solvents at reduced pressure. Purify the residue by preparative TLC (eluent Hex/AcOEt 8/2). Alcohol 16 is obtained as a colorless oil (40 mg, 80%).

$[\alpha]_D^{20}$=−100° (CHCl₃, C=1.0)

¹H NMR (400 MHz, CDCl₃): 7.63 (d, J=16.0, 1H, CH=CH—COO), 7.48 (d, J=8.8, 1H, ArH), 6.89 (d, J=8.8, 1H, ArH) 6.38 (d, J=16.0, 1H, CH=CH—COO), 5.59 (br s, 1H, CH—O—C=O), 5.36 (t, J=6.6, 1H, (Me)C=CH), 3.84 (s, 3H, OMe), 3.58 (dd, J=11.2, 4.8, 1H, CHH—OH), 3.43 (dd, J=11.2, 5.6, 1H, CHH—OH), 3.32 (s, 3H, OMe), 3.20 (dd, J=11.5, 2.8, 1H, CH—OMe), 2.37 (t, J=11.5, 1H, CH—C(Me)=C), 2.15-1.95 (m, 3H), 1.75-1.35 (m, 6H), 1.62 (s, 3H, Me—C=CH), 1.26-1.22 (m, 2H, CH₂—CH(Me)₂), 0.88 & 0.87 (2 d, J=6.6, 6H, CH(Me)₂).

¹³C NMR (100 MHz, CDCl₃): 166.9, 161.3, 144.3, 133.8, 129.7, 128.9, 127.3, 116.1, 114.2, 80.5, 66.7, 66.4, 57.1, 55.3, 50.9, 40.8, 38.8, 33.9, 28.1, 27.7, 25.6, 23.1, 22.5, 22.4.

c—Synthesis of Compound 17:

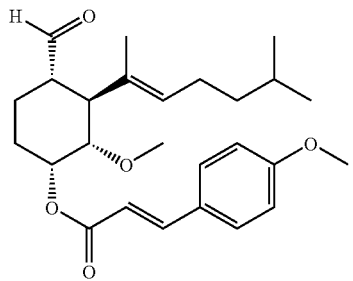

Add the Dess-Martin Periodinane (220 μL, 0.105 mmol, 15% solution, 1.5 eq) to a solution of alcohol 16 (30 mg, 0.070 mmol) in CH₂Cl₂ (1 mL). Stir the solution overnight, then stop the reaction by adding, in succession, saturated aqueous solution of NaHCO₃ (1 mL) then saturated aqueous solution of Na₂S₂O₃ (1 mL). After extraction with CH₂Cl₂ and evaporation of the solvents at reduced pressure, purify the residue by preparative TLC (eluent Hexane/AcOEt 9/1). Aldehyde 17 is obtained as a colorless oil (26 mg, 87%).

HRMS (FAB) m/z found 430.2727. calcd for C₂₆H₃₆O₅ m/z: 430.2719.

¹H NMR (400 MHz, CDCl₃): 9.49 (d, J=3.6, 1H, CHO), 7.65 (d, J=16.0, 1H, CH=CH—COO), 7.49 (d, J=8.8, 1H, ArH), 6.90 (d, J=8.8, 1H, ArH) 6.40 (d, J=16.0, 1H, CH=CH—COO), 5.58 (br s, 1H, CH—O—C=O), 5.36 (t, J=6.8, 1H, (Me)C=CH), 3.85 (s, 3H, OMe), 3.35 (s, 3H, OMe), 3.24 (dd, J=10.8, 2.8, 1H, CH—OMe), 2.79 (t, J=10.8, 1H, CH—C(Me)=CH), 2.38 (tt, J=10.8, 3.8, 1H, CH—CHO), 2.15 (dq, J=15.1, 3.8, 1H, CHH—CH(CHO)), 2.02 (m, 2H, C=CH—CH₂), 1.75 (m, 1H), 1.62 (s, 3H, Me—C=CH), 1.61-1.47 (m, 3H, CH(Me)₂ & CH₂—CH(O—C=O)), 1.20 (q, J=7.6, 2H, CH₂—CH(Me)₂), 0.87 & 0.85 (2 d, J=6.5, 6H, CH(Me)₂).

¹³C NMR (100 MHz, CDCl₃): 203.2, 166.8, 161.4, 144.7, 131.8, 130.0, 129.8, 127.2, 115.8, 114.3, 80.1, 66.4, 57.3, 55.4, 51.1, 47.9, 38.6, 27.6, 27.5, 25.7, 22.5, 22.4, 20.1, 12.9.

EXAMPLE 6

Synthesis of 2(S)-3(S)-4(S)-3-(1,5-dimethyl-hex-1-enyl)-2-methoxy-4-(2,2,2-trifluoro-1-hydroxy-1-trifluoromethyl-ethyl)-cyclohexanone (Compound 18 in FIG. 1)

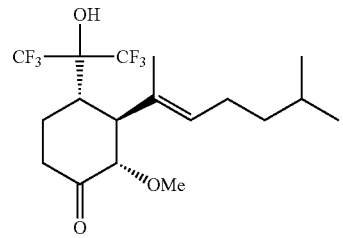

Treat diketone 12 (10 mg, 30 μmol), in solution in THF (0.3 mL), with CF₃SiMe₃ (5 μL, 33 μmol, 1.1 eq) and TBAF (3 μL, 0.1 eq) at 0° C. After 1 h at this temperature, hydrolyze the mixture by adding 1N HCl solution. After extraction with ethyl acetate, combine the organic phases, dry over anhydrous magnesium sulfate and evaporate the solvents. Purify the residue obtained by preparative TLC (CyH/AcOEt:8/2). Compound 18 is obtained in the form of a colorless oil (3 mg, 25%).

¹H NMR (400 MHz, CDCl₃): 5.45 (t, J=7.0, 1H, C=CH), 5.19 (s, 1H, OH), 3.57 (d, J=8.6, 1H, CH—OMe), 3.39 (s, 3H, OMe), 2.96 (t, J=8.6, 1H, CH—C(Me)=CH), 2.74 (m, 1H, CH—C(CF₃)₂OH), 2.55 (dt, J=14.0, 4.4, 1H, CHH—CO), 2.39 (td, J=14.0, 5.3, 1H, CHH—CO), 2.26 (m, 1H, C=O—CH₂—CHH), 2.06 (q, J=7.0, 2H, CH₂—CH=C), 1.95 (m, 1H, C=O—CH₂—CHH), 1.77 (s, 3H, Me), 1.55 (m, 1H, CH(Me)₂), 1.23 (m, 2H, CH₂—CH(Me)₂), 0.88 (d, J=7.0, 6H, (Me)₂).

EXAMPLE 7

Determination of the Enantiomeric Excess of Cyclohexanone 6 (Shown in FIG. 2) by NMR by Forming a Mosher Ester

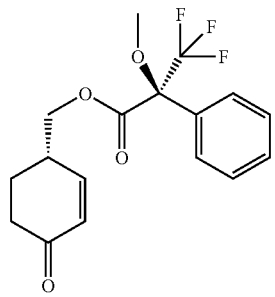

Treat cyclohexenone 6 (12 mg, 50 μmol), in solution in THF, with TBAF (50 μL, 1M in THF, 1 eq) for 1 h at RT. Stop the reaction by hydrolysis (NH₄Cl), then extract with AcOEt. Dry the organic phases (MgSO₄), then evaporate the solvents at reduced pressure. Dissolve the residue obtained in CH₂Cl₂ (0.5 mL), then add Et₃N (8 μL, 60 μmol) and DMAP (8 mg, 60 μmol), as well as a solution of (S)-(−)-α-methoxy-α-(trifluoromethyl)benzylacetyl chloride (prepared from (−)-MPTA (23.4 mg, 100 µmol) and (COCl)$_2$ (9 µL, 100 µmol) in CH$_2$Cl$_2$ (1 mL), 2 h at RT). Stir the solution obtained overnight at RT, then hydrolyze (NH$_4$Cl) and extract with AcOEt. Dry the organic phases (MgSO$_4$) then evaporate the solvents at reduced pressure. Filter the residue obtained on a bed of silica (eluent CyH/AcOEt 8/2). The Mosher ester is obtained in the form of a colorless oil (9 mg, 50%) at diastereomeric ratio of 91/9 ($^{19}$F NMR).

$^1$H NMR (400 MHz, CDCl$_3$): 7.50 (m, 2H, ArH), 7.45-7.40 (m, 3H, ArH), 6.75 (ddd, J=10.2, 2.3, 1.5, 1H, CH=CH—C=O), 6.06 (dd, J=10.2, 2.4, 1H, CH=CH—C=O), 4.34 (m, 2H, CH$_2$—OCO), 3.54 (s, 3H, OMe), 2.86 (m, 1H, CH—CH$_2$—OCO), 2.52 (dt, J=16.8, 4.6, 1H, C=O—CHH), 2.36 (ddd, J=16.8, 12.6, 5.1, 1H, C=O—CHH), 2.10 (dm, J=13.0, 1H, C=O—CH$_2$—CHH), 1.78 (tdd, J=13.0, 9.8, 4.5, 1H, C=O—CH$_2$—CHH).

$^{19}$F NMR (376 MHz, C$_6$D$_6$): major diastereomer: −69.329 minor diastereomer: −69.393. e.e.=82%

EXAMPLE 8

Synthesis of (E)-2-bromo-6-methyl-hept-2-ene: This Compound Occurs in the Preparation of Compound 8 (Shown in FIG. 2), as Described in Example 1e a—Preparation of Acetone Trisylhydrazone:

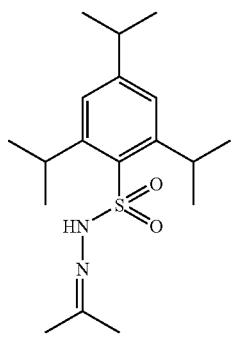

Add hydrazine (5 mL, 103.1 mmol, 2 eq.) dropwise to 2,4,6-triisopropylbenzenesulfonyl chloride (15 g, 53.7 mmol) in 30 mL of THF at −10° C. Stir the reaction mixture at 0° C. for 3 h, then hydrolyze. Wash the organic phase 3 times with 10 mL of saturated solution of sodium chloride, then dry over Na$_2$SO$_4$. After evaporation of the solvent, dry the solid obtained for 1 h under vacuum (10 mmHg) over P$_2$O$_5$. 14.69 g of 2,4,6-triisopropylbenzenesulfonyl hydrazine is obtained as a white solid. Add acetone (50 mL, 12 eq.) to the 2,4,6-triisopropylbenzenesulfonyl hydrazine (14.69 g, 53.4 mmol). Stir the reaction mixture for 30 min at RT. Evaporate the excess acetone and recrystallize the solid obtained from a methanol/water mixture. After drying the white crystals obtained, 12.6 g (69%) of trisylhydrazone derivative of acetone is obtained.

F=148° C. (lit. F=136-138° C., Arlington, R. M.; Barrett, A. G. *J. Chem. Soc., Perkin Trans.*, 1, 1981, 2848-2863)

$^1$H NMR (400 MHz, CDCl$_3$): 7.17 (s, 2H, Ar—H), 7.06 (brs, 1H, NH), 4.24 (hept, J=6.8, 2H, ortho CH(Me)$_2$), 2.90 (hept, J=6.8, 1H, para CH(Me)$_2$), 1.99 (s, 3H, Me—C=N), 1.78 (s, 3H, Me—C=N), 1.27 (d, J=6.8, 12H, ortho CH(Me)$_2$), 1.25 (d, J=6.8, 1H, para CH(Me)$_2$).

b—Synthesis of (E)-2-bromo-6-methyl-hept-2-ene:

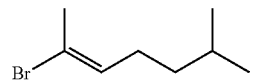

Dissolve the trisylhydrazone derivative of acetone (8.0 g, 23.7 mmol) in 70 mL of DME at −78° C. Add butyllithium (29.6 mL, 47.4 mmol, 2 eq.) dropwise. Stir the mixture at −60° C. for 10 min, cool to −78° C., then add 1-iodo-3-methylbutane (3.13 mL, 23.7 mmol, 1 eq.) dropwise. Stir the mixture overnight at −65° C., cool to −78° C., then treat successively with TMEDA (12.5 mL, 82.3 mmol, 3.5 eq.), then BuLi (16.3 mL, 26.1 mmol, 1.1 eq.). Stir this mixture for 20 min at −78° C., then heat to 0° C. and maintain at this temperature until evolution of nitrogen ceases (~5 min). Then cool the reaction mixture to −78° C. and add 1,2-dibromoethane (6.6 mL, 35.5 mmol, 1.5 eq). Heat the mixture slowly to 0° C., then hydrolyze with aqueous NaCl. After extraction (Et$_2$O) and washing (twice with water then once with saturated NaCl solution), dry the solution over MgSO$_4$ and evaporate. Then chromatograph the residue on silica gel (eluent: cyclohexane). The brominated derivative (E)-2-bromo-6-methyl-hept-2-ene is obtained in the form of a slightly yellow oil (2.5 g, 57%).

$^1$H NMR (400 MHz, CDCl$_3$): 5.82 (t, J=7.4, 1 H, CH$_2$—CH=C), 2.21 (s, 3 H, Me), 2.00 (q, J=7.7, 2 H, CH$_2$—CH=C), 1.54 (hept, J=6.7, 1 H, CH(Me)$_2$), 1.25 (q, J=7.5, 2 H, CH$_2$—CH(Me)$_2$), 0.88 (d, 6 H, J=6.8, (CH$_3$)$_2$CH).

$^{13}$C NMR (100 MHz, CDCl$_3$): 132.6 (C=CH), 118.9 (C=C), 38.1 (CH$_2$CH(Me)$_2$), 27.5 (CH(Me)$_2$), 27.4 (CH$_3$—C=C), 23.1 (C=C—CH$_2$), 22.4 (CH(CH$_3$)$_2$).

EXAMPLE 9

Formulation Examples

1) Oral Route:
(a) Tablets of 0.2 g:

| | |
|---|---|
| Compound of Example 1 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Oral Suspension in 5-ml Ampoules:

| | |
|---|---|
| Compound of Example 3 | 0.001 g |
| Glycerol | 0.500 g |
| Sorbitol at 70% | 0.500 g |
| Sodium saccharinate | 0.010 g |
| Methyl parahydroxybenzoate | 0.040 g |
| Aroma | qs |
| Purified water | qsf 5 ml |

(c) Tablets of 0.8 g:

| | |
|---|---|
| Compound of Example 1 | 0.250 g |
| Compound of Example 2 | 0.250 g |
| Pregelatinized starch | 0.100 g |
| Microcrystalline cellulose | 0.115 g |
| Lactose | 0.075 g |
| Magnesium stearate | 0.010 g |

(d) Oral Suspension in 10-ml Ampoules:

| | |
|---|---|
| Compound of Example 4 | 0.05 g |
| Glycerol | 1.000 g |
| Sorbitol at 70% | 1.000 g |
| Sodium saccharinate | 0.010 g |
| Methyl parahydroxybenzoate | 0.080 g |
| Aroma | qs |
| Purified water | qsf 10 ml |

2) Topical Route:
(a) Unguent:

| | |
|---|---|
| Compound of Example 6 | 0.020 g |
| Isopropyl myristate | 81.700 g |
| Fluid vaseline oil | 9.100 g |
| Silica ("Aerosil 200" marketed by DEGUSSA) | 9.180 g |

(b) Unguent:

| | |
|---|---|
| Compound of Example 5 | 0.150 g |
| Compound of Example 6 | 0.150 g |
| White vaseline, codex | 100 g |

(c) Non-Ionic Water-in-Oil Cream:

| | |
|---|---|
| Compound of Example 5 | 0.100 g |
| Mixture of emulsive lanolin alcohols, waxes and oils ("Anhydrous Eucerine" marketed by BDF) | 39.900 g |
| Methyl parahydroxybenzoate | 0.075 g |
| Propyl parahydroxybenzoate | 0.075 g |
| Sterile demineralized water | qsf 100 g |

(d) Lotion:

| | |
|---|---|
| Compound of Example 6 | 0.100 g |
| Polyethylene glycol (PEG 400) | 69.900 g |
| Ethanol at 95% | 30.000 g |

(e) Hydrophobic Unguent:

| | |
|---|---|
| Compound of Example 1 | 0.200 g |
| Compound of Example 5 | 0.100 g |
| Isopropyl mirystate | 36.400 g |
| Silicone oil ("Rhodorsil 47 V 300" marketed by RHONE-POULENC) | 36.400 g |
| Beeswax | 13.600 g |

-continued

| | |
|---|---|
| Silicone oil ("Abil 300.000 cst" marketed by GOLDSCHMIDT) | 100 g |

(f) Non-Ionic Oil-in-Water Cream:

| | |
|---|---|
| Compound of Example 2 | 0.500 g |
| Cetyl alcohol | 4.000 g |
| Glycerol monostearate | 2.500 g |
| Stearate of PEG 50 | 2.500 g |
| Shea butter | 9.200 g |
| Propylene glycol | 2.000 g |
| Methyl parahydroxybenzoate | 0.075 g |
| Propyl parahydroxybenzoate | 0.075 g |
| Sterile demineralized water | 100 g |

3) Intralesional Route:
(a) Prepare the Following Composition:

| | |
|---|---|
| Compound of Example 6 | 0.002 g |
| Ethyl oleate qsf | .10 g |

For treatment of malignant melanoma, administer the composition to an adult patient by injection at a frequency of 1 to 7 times per week for 1 to 12 months.

(b) Prepare the Following Composition:

| | |
|---|---|
| Compound of Example 4 | 0.050 g |
| Olive oil | qsf 2 g |

For the treatment of basal cell carcinoma, administer the composition to an adult patient by injection at a frequency of 1 to 7 times per week for 1 to 12 months.

(c) Prepare the Following Composition:

| | |
|---|---|
| Compound of Example 3 | 0.1 mg |
| Sesame oil | qsf 2 g |

For the treatment of spinocellular carcinoma, administer the composition to an adult patient by injection at a frequency of 1 to 7 times per week for 1 to 12 months.

(d) Prepare the Following Composition:

| | |
|---|---|
| Compound of Example 2 | 0.001 mg |
| Methyl benzoate | qsf 10 g |

For the treatment of colonic carcinoma, administer the composition to an adult patient by injection at a frequency of 1 to 7 times per week for 1 to 12 months.

4) Intravenous Route:
(a) Prepare the Following Injectable Composition:

| | |
|---|---|
| Compound of Example 2 | 0.001% |
| Solution of sodium bicarbonate at 1.4% | 2% |
| Ethanol | 1% |
| Solution of NaCl at 0.9% | qsf 100 |

What is claimed is:

1. A compound having the following formula (I):

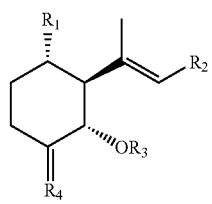

in which:

R₁ is a radical of structure (a) or of structure (b):

(a):

(b):

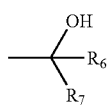

wherein R₅, R₆ and R₇ are as defined below;

R₂ is a lower alkyl radical having 1 to 5 carbon atoms;

R₃ is a lower alkyl radical having 1 to 5 carbon atoms;

R₄ is a radical of structure (c), bound by a single bond to the cyclohexane from which it depends:

(c):

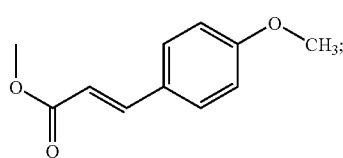

or R₄ is an oxygen atom bound by a double bond to the cyclohexane from which it depends;

R₅ is a hydrogen atom or a methyl radical or a trifluoromethyl radical; and

R₆ and R₇ represent, independently of each other, a hydrogen atom or a trifluoromethyl radical, or salt or isomer thereof.

2. The compound as defined by claim 1, bearing at least one methyl, ethyl, propyl, isopropyl, n-propyl, butyl, isobutyl, n-butyl, pentyl, isopentyl or n-pentyl radical substituent.

3. The compound as defined by claim 1, wherein R₂ is a 3-methylbutyl radical and/or R₃ is a methyl radical.

4. The compound as defined by claim 1, selected from the group consisting of:
1) 2(S)-3(S)-4(S)-3-(1,5-Dimethyl-hex-1-enyl)-4-hydroxymethyl-2-methoxy-cyclohexanone;
2) 1(S)-2(S)-3(S)-2-(1,5-Dimethyl-hex-1-enyl)-3-methoxy-4-oxo-cyclohexanecarbaldehyde;
3) 2(S)-3(S)-4(S)-3-(1,5-Dimethyl-hex-1-enyl)-2-methoxy-4-(2,2,2-trifluoro-acetyl)-cyclohexanone;
4) 2(S)-3(S)-4(S)-4-Acetyl-3-(1,5-dimethyl-hex-1-enyl)-2-methoxy-cyclohexanone;
5) 1(R)-2(S)-3(S)-4(S)-3-(4-Methoxy-phenyl)-acrylic acid 3-(1,5-dimethyl-hex-1-enyl)-4-formyl-2-methoxy-cyclohexyl ester;
6) 2(S)-3(S)-4(S)-3-(1,5-Dimethyl-hex-1-enyl)-2-methoxy-4-(2,2,2-trifluoro-1-hydroxy-1-trifluoromethylethyl)-cyclohexanone, and mixtures thereof.

5. A pharmaceutical composition comprising at least one compound as defined by claim 1, formulated into a pharmaceutically acceptable carrier therefor.

6. A pharmaceutical composition as defined by claim 5, comprising from 0.0001 wt. % to 20 wt. % relative to the total weight of the composition of said at least one compound.

7. A cosmetic composition comprising at least one compound as defined by claim 1, formulated into a cosmetically acceptable carrier therefor.

8. The cosmetic composition as defined by claim 1, comprising from 0.0001 wt. % to 3 wt. % relative to the total weight of the composition of said at least one compound.

9. A method for the inhibition of angiogenesis comprising administering to a subject in need of such inhibition, an effective angiogenesis-inhibiting amount of a pharmaceutical composition comprising at least one compound having the following formula (I):

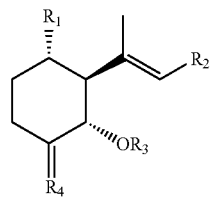

in which:

R₁ is a radical of structure (a) or of structure (b):

(a):

(b):

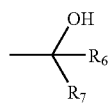

wherein R₅, R₆ and R₇ are as defined below

R₂ is a lower alkyl radical having 1 to 5 carbon atoms;

R₃ is a lower alkyl radical having 1 to 5 carbon atoms;

R₄ is a radical of structure (c), bound to the cyclohexane from which it depends;

(c):

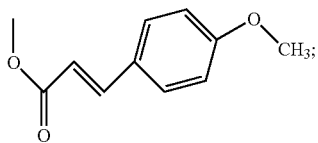

or R₄ is an oxygen atom bound by a double bond to the cyclohexane from which it depends;

$R_5$ is a hydrogen atom or a methyl radical or a triflurom-ethyl radical; and $R_6$ and $R_7$ represent independently of each other, a hydrogen atom or a trifluoromethyl radical, or salt or isomer thereof;

formulated into a pharmaceutically acceptable carrier therefor.

10. A method for the inhibition of the angiogenesis of rosacea comprising administering to a subject in need of such inhibition an effective angiogenesis-inhibiting amount of a pharmaceutical composition comprising at least one compound having the following formula (I):

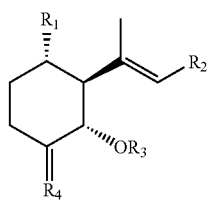

(I)

in which:
$R_1$ is a radical of structure (a) or of structure (b):

(a):

(b):

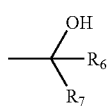

wherein $R_5$, $R_6$ and $R_7$ are as defined below
$R_2$ is a lower alkyl radical having 1 to 5 carbon atoms;
$R_3$ is a lower alkyl radical having 1 to 5 carbon atoms;
$R_4$ is a radical of structure (c), bound to the cyclohexane from which it depends;

(c):

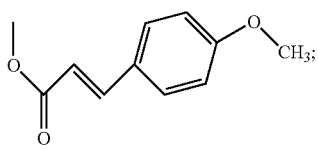

or R₄ is an oxygen atom bound by a double bond to the cyclohexane from which it depends;

$R_5$ is a hydrogen atom or a methyl radical or a triflurom-ethyl radical; and $R_6$ and $R_7$ represent independently of each other, a hydrogen atom or a trifluoromethyl radical, or salt or isomer thereof;

formulated into a pharmaceutically acceptable carrier therefor.

11. A method for the inhibition of angiogenesis in the skin or scalp of a subject in need of such inhibition comprising topically applying to said skin or scalp an effective angiogenesis-inhibiting amount of a cosmetic composition comprising at least one compound having the following formula (I):

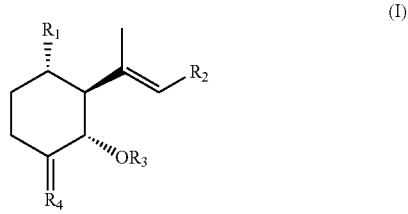

(I)

in which:
$R_1$ is a radical of structure (a) or of structure (b):

(a):

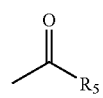

(b):

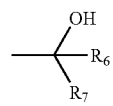

wherein $R_5$, $R_6$ and $R_7$ are as defined below;
$R_2$ is a lower alkyl radical having 1 to 5 carbon atoms;
$R_3$ is a lower alkyl radical having 1 to 5 carbon atoms;
$R_4$ is a radical of structure (c), bound to the cyclohexane from which it depends;

(c):

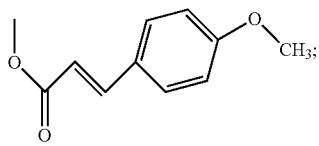

or R₄ is an oxygen atom bound by a double bond to the cyclohexane from which it depends;

$R_5$ is a hydrogen atom or a methyl radical or a triflurom-ethyl radical; and $R_6$ and $R_7$ represent independently of each other, a hydrogen atom or a trifluoromethyl radical, or salt or isomer thereof;

formulated into a cosmetically acceptable carrier therefor.

* * * * *